(12) United States Patent
Coudyzer

(10) Patent No.: US 10,543,311 B2
(45) Date of Patent: Jan. 28, 2020

(54) METHODS AND TOOLS RELATING TO THE ADMINISTRATION OF CONTRAST MEDIUM

(71) Applicant: Medicor International NV, Rotselaar (BE)

(72) Inventor: Walter Coudyzer, Linden (BE)

(73) Assignee: MEDICOR INTERNATIONAL NV, Rotselaar (BE)

(*) Notice: Subject to any disclaimer, the term of this patent is extended or adjusted under 35 U.S.C. 154(b) by 932 days.

(21) Appl. No.: 14/916,710

(22) PCT Filed: Sep. 18, 2014

(86) PCT No.: PCT/EP2014/069928
§ 371 (c)(1),
(2) Date: Mar. 4, 2016

(87) PCT Pub. No.: WO2015/040128
PCT Pub. Date: Mar. 26, 2015

(65) Prior Publication Data
US 2016/0213833 A1    Jul. 28, 2016

(30) Foreign Application Priority Data
Sep. 19, 2013   (NL) .................................. 2011470

(51) Int. Cl.
*A61B 5/00* (2006.01)
*A61M 5/00* (2006.01)
*A61B 6/00* (2006.01)
*A61B 5/024* (2006.01)
*A61M 31/00* (2006.01)

(52) U.S. Cl.
CPC ............. *A61M 5/007* (2013.01); *A61B 5/024* (2013.01); *A61B 6/481* (2013.01); *A61M 31/005* (2013.01)

(58) Field of Classification Search
CPC ................. A61M 5/007; A61M 5/1723; A61M 5/16877; A61M 5/168; A61M 31/005; A61M 2205/50; A61B 5/024; A61B 6/481; A61B 6/03; G16H 40/63; G06F 19/321
See application file for complete search history.

(56) References Cited

U.S. PATENT DOCUMENTS

| | | | |
|---|---|---|---|
| 5,583,902 A | 12/1996 | Bae et al. | |
| 5,687,208 A | 11/1997 | Bae et al. | |
| 7,453,975 B2 | 11/2008 | Haras et al. | |
| 7,672,711 B2 | 3/2010 | Haras et al. | |
| 7,706,504 B2 | 4/2010 | Ohishi | |
| 8,483,799 B2 | 7/2013 | Böing et al. | |
| 2010/0113887 A1* | 5/2010 | Kalafut .................. | A61M 5/007 600/300 |
| 2010/0114064 A1* | 5/2010 | Kalafut .................. | A61B 5/411 604/508 |
| 2013/0041257 A1 | 2/2013 | Nemoto | |
| 2013/0109966 A1 | 5/2013 | Assmann et al. | |

FOREIGN PATENT DOCUMENTS

| | | |
|---|---|---|
| CN | 101015457 B | 11/2011 |
| JP | 2012-254359 A | 12/2012 |
| WO | 2007/062315 A2 | 5/2007 |
| WO | 2008/082937 A2 | 7/2008 |

OTHER PUBLICATIONS

Bae et al. (2008) "Contrast Enhancement in Cardiovascular MDCT: Effect of Body Weight, Height, Body Surface Area, Body Mass Index, and Obesity," Am. J. Roentgenol. 190(3):777-784.
Lu et al. (2010) "What is the best contrast injection protocol for 64-row multi-detector cardiac computed tomography?" Eur. J. Radiol. 75(2):159-165.
Yanaga et al. (2010) "Contrast material injection protocol with the dose adjusted to the body surface area for MDCT aortography," Am. J. Roentgenol. 194(4):903-908.
International Preliminary Report on Patentability corresponding to International Patent Application No. PCT/EP2014/069928, dated Jan. 11, 2016.
International Search Report with Written Opinion corresponding to International Patent Application No. PCT/EP2014/069928, dated Nov. 18, 2014.
Written Opinion of the International Preliminary Examining Authority corresponding to Application No. PCT/EP/2014/069928, dated Oct. 2, 2015.
Voroiskiy F.S., (2006) "Introduction to Modern Information and Telecommunication Technologies in terms and figures," Informatics. Encyclopedic systematized dictionary, pp. 19, 211, 214, 221-222, 231-233.

* cited by examiner

*Primary Examiner* — Joel Lamprecht
(74) *Attorney, Agent, or Firm* — Lathrop Gage LLP; James H. Velema, Esq.

(57) ABSTRACT

Envisaged herein are methods for determining the optimal volume of contrast medium to be administered to a patient. More particularly, the methods envisaged herein comprise the steps of (a) measuring one or more patient-specific physiological parameters, said one or more patient-specific physiological parameters comprising at least the patient's heart rate; and (b) determining the optimal volume of contrast medium based on the patient-specific physiological parameters determined under (a).

15 Claims, No Drawings

METHODS AND TOOLS RELATING TO THE ADMINISTRATION OF CONTRAST MEDIUM

RELATED APPLICATIONS

This application is a 35 U.S.C. § 371 filing of International Application No. PCT/EP2014/069928, filed Sep. 18, 2014, which claims priority to Netherlands Patent Application No. N2011470, filed Sep. 19, 2013, each of which are incorporated herein by reference in their entireties.

TECHNICAL FIELD OF THE INVENTION

The application provides methods and tools relating to the administration of contrast medium. More particularly the application provides methods and tools for determining the optimal volume of contrast medium to be administered to a patient.

BACKGROUND OF THE INVENTION

Medical imaging is the technique and process used to create images of the internal aspects of the human body (or parts and function thereof) for clinical purposes (medical procedures seeking to reveal, diagnose, or examine disease) or medical science (including the study of normal anatomy and physiology). Imaging methods include X-ray examinations, magnetic resonance imaging (MR), ultrasound, positron-emission tomography (PET), spectroscopy and the like.

When employing these methods, the use of a contrast medium comprising a agent is generally required, since administration of a contrast agent to a scan subject not only produces an improvement in image quality, but also contrast can be achieved due to properties of the contrast medium. Typically, the amount of contrast medium administered is a standard amount, which is determined by the region of the body to be scanned.

The use of intravenous contrast media has been associated with a wide range of adverse reactions, which include nausea and vomiting; a metallic taste in the mouth; flu-like symptoms; mild to severe allergic reactions (anaphylactic reactions); and even renal toxicity.

At the same time, in some cases the amount of contrast medium that is used is experienced to be insufficient to provide enough visualization of all the bodily structures, thereby preventing the radiologist from making an accurate diagnosis.

U.S. Pat. No. 8,483,799, JP2012/254359 and describe methods and systems for imaging the heart, wherein the heart rate of the patient is measured during the administration of the contrast agent. Indeed, it is known that for the detection of coronary disease using a CT scan, the heart-rate is ideally below 65.

CN1010015457 describes a system wherein the heartbeat is used to determine the starting instant of the scan.

US2013/0109966 describes systems for optimizing the image quality of a scan over a prolonged period of time.

SUMMARY OF THE INVENTION

It is the object of the present application to provide methods for determining the optimal volume of contrast medium to be administered to a patient prior to administration. In particular embodiments, the methods envisaged herein have the advantage that they ensure that enough contrast medium will be administered to provide an accurate diagnosis while the number of adverse reactions that said contrast medium causes to a patient is reduced.

It has been established that the optimal volume of contrast medium to be administered can be established based on patient-specific physiological parameters, and most particularly, based on the patient's heart rate. Accordingly, the application provides methods for determining the optimal volume of contrast medium to be administered to a patient based on the patient's heart rate. In particular embodiments, the methods comprise the steps of: determining one or more patient-specific physiological parameters, said one or more patient-specific physiological parameters comprising at least the patient's heart rate and calculating the optimal volume of contrast medium based on said one or more patient-specific physiological parameters. In particular embodiments, the methods envisage determining the heart rate and one or more additional physiological parameters of the patient. In particular embodiments of the methods envisaged herein, the additional patient-specific physiological parameters include length and weight of the patient. In further particular embodiments, the length and weight of the patient are used to determine the Body Surface Area (BSA) of the patient, and both the BSA and the heart rate of the patient are used to determine the optimal volume of contrast medium. Additionally or alternatively, the patient-specific parameters can include age, gender, estimated glomerular filtration rate (eGFR) and cardiac output (CO). Additionally or alternatively, the calculation of the optimal volume of contrast medium further comprises taking into account one or more non-patient specific parameters, such as scanner type and/or tube voltage of the scanner to be used for imaging.

In particular embodiments, the optimal volume of contrast medium is determined starting from an initial volume of contrast medium, which is further adjusted based on said one or more patient-specific physiological parameters. In further particular embodiments the method comprises: measuring one or more patient-specific physiological parameters, said one or more patient-specific physiological parameters comprising at least the patient's heart rate; calculating an initial volume of contrast medium, and; adjusting the initial volume of contrast medium on the basis of the patient's heart rate, thereby determining the optimal volume of contrast medium, is provided.

In particular embodiments, said initial volume of contrast medium is determined based on the BSA of said patient and is then adjusted based on the heart rate of said patient. In particular embodiments of the methods envisaged herein the initial volume of contrast medium is decreased in volume, if said patient's heart rate is below a predetermined threshold level and the initial volume of contrast medium is increased in volume, if said patient's heart rate is above said predetermined threshold level.

In further particular embodiments the methods comprise taking into account threshold levels for determining the amount of volume by which the initial volume of contrast medium is to be decreased or increased. In particular embodiments, the methods involve taking into account at least two predetermined threshold levels, wherein the initial volume of contrast medium is decreased in volume if the patient's heart rate is below or equal to a first predetermined threshold level; and the initial volume of contrast medium is increased in volume if the patient's heart rate is above or equal to a second predetermined threshold level. The threshold levels can be determined by the skilled person. In particular embodiments, the first predetermined threshold level is chosen in the range of 50 to 60 beats-per-minute; in particular embodiments the second predetermined threshold level is chosen in the range of 61 to 71 beats-per-minute. In particular embodiments where both threshold levels are used, the initial volume of contrast medium is not adjusted if the patient's heart rate is situated between the first and second threshold levels.

The decrease or increase in volume of contrast medium to be applied can be determined by the skilled person. In particular embodiments, the decrease in volume of the initial volume of contrast medium is chosen in the range of 1 to 19 ml. In particular embodiments, the increase in volume of the initial volume of contrast medium is chosen in the range of 1 to 40 ml.

In particular embodiments of the methods envisaged herein, the initial volume of contrast medium is further adjusted based on one or more of the following patient-derived quotients: body mass index; Ideal body weight; lean body weight; adjusted body weight and body surface area. In particular embodiments, the patient's height and weight are used to determine the patient's body surface area and the body surface area is used to determine the initial volume of contrast medium.

In particular embodiments of the methods envisaged herein, the optimal volume of contrast medium obtained in step (c) is further diluted.

In particular embodiments, the contrast medium comprises a radiocontrast agent, and may be an iodine-based contrast medium.

The present application also encompasses tools, such as devices such as injectors of contrast media and/or controllers for injectors of contrast media and computer programs (which may be provided on computer-readable media) for driving such devices, which are adjusted to carry out the methods as envisaged herein.

Thus, in particular embodiments, the application provides a controller for a device for injecting contrast medium into a patient using an injector, said device or controller comprising an input means allowing input of one or more patient-specific physiological parameters, said one or more patient-specific physiological parameters comprising at least the patient's heart rate; a processer configured to calculate the optimal volume of contrast medium based on said one or more patient-specific physiological parameters; and a connection to the injector configured to control the volume of contrast medium to be injected into the patient prior to administration, based on said optimal volume calculated by said processor.

In particular embodiments of the controller, the additional patient-specific physiological parameters include length and weight of the patient. In further particular embodiments the length and weight of the patient are used to determine the Body Surface Area (BSA) of the patient and said optimal volume of contrast medium is calculated based both on the BSA and the heart rate of said patient.

In particular embodiments of the controller the calculation of said optimal volume of contrast medium comprises starting from an initial volume of contrast medium and adjusting said volume based on said one or more patient-specific physiological parameters. More particularly, the processor can make use of ranges with threshold values based on which the initial volume is either increased or decreased. In particular embodiments, the processor makes use of ranges with threshold values based on which the initial volume is either increased or decreased and wherein said calculation is based on at least two predetermined threshold values, whereby the initial volume of contrast medium is decreased when the heart rate of the patient is lower or equal to the first previously determined limit value and whereby the initial volume of contrast medium is increased when the heart rate of the patient is higher or equal to the second threshold value. In further particular embodiments, the first predetermined threshold level is chosen in the range of 50 to 60 beats-per-minute and wherein the second predetermined threshold level is chosen in the range of 61 to 71 beats-per-minute. For example, the decrease in volume of the initial volume of contrast medium is chosen in the range of 1 to 19 ml and the increase in volume of contrast medium is selected to be in the range of 1 to 40 ml.

In particular embodiments of the controller, the optimal volume of contrast medium is further calculated based on one or more patient-derived quotients selected from body mass index; Ideal body weight; lean body weight; adjusted body weight and body surface area. Additionally or alternatively, the patient-specific parameters comprise one or more parameters selected from age, gender, estimated glomerular filtration rate (eGFR) and cardiac output (CO). In particular embodiments, the processor further takes into account one or more non-patient-specific parameters to calculate said optimal volume of contrast medium, said one or more non-patient-specific parameters being selected from the tube-voltage of the scanner instrument to be used for imaging and the type of scanner used for imaging.

The application further provides contrast delivery systems comprising a controller as described herein and an injector.

The application further envisages computer programs, comprising instructions to carry out the method of determining the optimal volume of contrast medium to be administered to a patient according to an embodiment envisaged herein. In particular embodiments, the computer program ensures the methods envisaged herein when loaded on a computer. More particularly, the application envisages computer-readable media, configured to drive a controller as described herein. In particular embodiments, the computer-readable medium comprises a computer program comprising instructions for carrying out, when loaded on a computer, a method for determining for determining the optimal volume of contrast medium to be administered to a patient prior to administration, comprising the steps of: (a) determining one or more patient-specific physiological parameters, said one or more patient-specific physiological parameters comprising at least the patient's heart rate; and (b) calculating the optimal volume of contrast medium based on said one or more patient-specific physiological parameters.

DETAILED DESCRIPTION OF THE INVENTION

Before the present methods used in the invention are described, it is to be understood that this invention is not limited to the specific methods, components, or devices as described herein, but also encompasses variations of such methods, components, and devices as can be envisaged by the skilled person based on the teaching provided herein. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

As used herein, the singular forms "a", "an", and "the" include both singular and plural referents unless the context clearly dictates otherwise. The terms "comprising", "comprises" and "comprised of" as used herein are synonymous with "including", "includes" or "containing", "contains", and are inclusive or open-ended and are used to refer to embodiments which do not exclude additional, non-recited members, elements or method steps but may include embodiments which "consist of" the recited members, elements or method steps, i.e. which do not include additional, non-recited members, elements or method steps. The recitation of numerical ranges by endpoints includes all numbers and fractions subsumed within the respective ranges, as well as the recited endpoints. The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed. All documents cited in the present specification are hereby incorporated by reference in their entirety.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

By means of further guidance, definitions for the terms used in the description are included to better appreciate the teaching of the present invention.

According to a first aspect the application provides methods for determining the optimal volume of contrast medium to be administered to a patient prior to administration. Indeed it has been found that the patient's heart rate at the time of administration will significantly affect to what extent the contrast medium will be effectively distributed throughout the body, and more particularly to the region of the body of interest.

As used herein, the term "contrast medium" refers to a substance used for injection into a patient to enhance the contrast of structures of fluids within the body, in a medical imaging procedure. A contrast medium will comprise a contrast agent at a particular density. More particularly as referred to herein, contrast medium refers to undiluted contrast medium as supplied by the manufacturers. In particular embodiments, the contrast agent present in the contrast medium is a radio contrast agent, more particularly an iodine-containing agent as will be detailed below.

The methods of the present invention are aimed at determining the optimal volume of contrast agent to be administered for each patient, in order to ensure optimal image quality without jeopardizing the health of the patient. More particularly the methods of the present invention allow an automatic calculation of the optimal volume of contrast medium to be administered, prior to starting the imaging process.

The methods of the present invention thus comprise determining the optimal volume of contrast agent based on physiological parameters of the patient, which include the patient's heart-rate. In particular embodiments, the methods envisaged herein thus comprise the step of determining the patient's heart rate and determining the suitable volume of contrast medium to be administered based thereon. More particularly, the suitable volume of contrast medium to be administered is determined prior to the start of administration of the contrast medium to the patient. In particular embodiments, this implies that the volume of contrast medium to be administered does not need to be adjusted during administration and is thus fixed based on the methods disclosed herein.

The patient's heart rate may be determined based on available information (e.g. patient records, etc). However, in particular embodiments, the envisaged methods include a measuring step of the patient's heart rate.

As used herein, the term "heart rate" refers to the amount of heartbeats, particularly, the term heart rate refers to the number of heartbeats per unit of time. More particularly, the term heart rate refers to the number of heartbeats-per-minute.

The patient-specific physiological parameters, including the heart-rate may be measured using any techniques, apparatus and methods known in the art. More particularly, it is well-established that the heart rate can be monitored at different points of the body, such as but not limited to the ventral aspect of the wrist on the side of the thumb (radial artery), the ulnar artery, the neck (carotid artery), the inside of the elbow, or under the biceps muscle (brachial artery), the groin (femoral artery), behind the medial malleolus on the feet (posterior tibial artery), at the middle of dorsum of the foot (dorsalis pedis), behind the knee (popliteal artery), over the abdomen (abdominal aorta), on the chest (apex of the heart), the temple (superficial temporal artery), the lateral edge of the mandible (facial artery) or the side of the head near the ear (posterior auricular artery). Depending on the location, the heart rate can be detected manually or by using specifically designed monitors such as a pulse-oximeter or an electrocardiograph (ECG).

The methods envisaged herein envisage determining the optimal volume of contrast medium based the heart rate of the patient. In particular embodiments, the determination of the optimal volume of contrast medium may further comprise one or more other patient-specific parameters. Additionally or alternatively, the determination of the optimal volume of contrast medium may further comprise one or more parameters related to the specifics of the imagining method.

Examples of envisaged patient-specific parameters are body weight (in air), body height, gender, age, residual lung volume, estimated glomerular filtration rate (eGFR), cardiac output (CO), skinfold volume, girth measurement, etc. . . . With regard to body weight and height it is envisaged that these can affect the volume envisaged for administration directly. The relationship between the optimal volume of contrast medium and body weight and height can be linear or non-linear and monotonic or non-monotonic. In particular embodiments, it is envisaged that these parameters need only be taken into consideration when they fall outside a given range. Similarly with regard to age, it is envisaged that this parameter may have a linear or non-linear relationship with the optimal volume of contrast medium to be administered. It is envisaged that for older patients, the risk of reduced heart function is taken into consideration, such that the volume of contrast medium is reduced. Gender may also be taken into consideration, whereby generally the optimal volume of contrast medium to be administered to males is higher than in females. It will of course be understood to the skilled person that, to the extent the method involves starting from an initial volume of contrast medium in order to adjust this so as to arrive at the optimal volume of contrast medium, it is envisaged that these parameters will no longer be taken into consideration if they have already played a role in the determination of the starting volume.

It is noted that these patient-specific parameters may be considered individually or may be used to determine one or more patient-derived quotients, which is used to determine the optimal volume of contrast medium, as will be detailed below.

As used herein, the term "residual lung volume" refers to the volume of air remaining in the lungs of a patient, after a maximal exhalation. As used herein, the term "skinfold measurement" refers to the measurement of the thickness of selected folds of skin using a special instrument (caliper). Particular skinfold measurements used in the present application include, the skinfold of the triceps; the skinfold of the biceps; the subscapular skinfold; the skinfold of the thigh; the iliac crest skinfold; the supraspinal skinfold; the abdominal skinfold; the calf skinfold; the chest skinfold; the skinfold in the axillae; the skinfold of the forearm and the skinfold of the back. In a particular embodiment, the abdominal skinfold; the iliac crest skinfold; the skinfold of the triceps; the skinfold of the chest or the skinfold of the thigh are used.

As used herein, the term "girth measurement" refers to the measurement of the circumference of a body part. Particular girth measurements used in the present application include, the girth of the neck; the forearm, the chest; the thigh; the abdomen; the waist; the gluteus and the hip. In a particular embodiment, the girth of the neck and the girth of the abdomen are used. In another particular embodiment, the girth of the neck, the girth of the waist and the girth of the hip are used. In another particular embodiment, the girth of the waist and the girth of the forearm are used.

The "estimated glomerular filtration rate (eGFR)" is a known parameter which provides an indication of kidney function. Where the eGFR is below that of a normally functioning kidney, it is envisaged that the amount of contrast medium should be reduced, in order to avoid toxic effects of the medium in the patient.

The cardiac output (CO) refers to the amount of blood that will be pumped through the hart per minute. In particular embodiments, this parameter can also be taken into consideration for determining the optimal volume of contrast agent. Indeed, the cardiac output of a patient can reflect factors which will also affect the ability of the heart to pump the contrast agent to the organ of interest other than the heart rate, such as e.g. malfunctioning of one or more heart valves.

In particular embodiments, the patient-specific physiological parameters are used to determine one or more patient-derived quotients. Examples of patient-derived quotients include but are not limited to Body mass index, Ideal body weight, Lean body weight; Adjusted body weight; Ponderal index; Body surface area, muscle mass, body fat percentage, body density.

In particular embodiments, the patient's height and weight are used to determine at least one of the following patient-derived quotients selected from Body mass index, Ideal body weight, Lean body weight; Adjusted body weight; Ponderal index; and Body surface area. In particular embodiments, one or more of these quotients is used to determine the initial volume of contrast medium. For instance, in particular embodiments, the patient's body weight and height is used to determine Body surface area (BSA). Methods for determining BSA based on body weight and height are known in the art and include but are not limited to the following algorithms (wherein W is weight expressed in kg; and wherein H is height expressed in cm):

$$BSA=[(\text{height} \times \text{weight})/3600]^{0.5}$$

$$BSA=0.007184 \times W^{0.425} \times H^{0.725}$$

$$BSA=0.024265 \times W^{0.5378} \times H^{0.3964}$$

$$BSA=0.0235 \times W^{0.51456} \times H^{0.42246}$$

$$BSA=0.03330 \times W^{(0.6157-0.0188\log 10W)} \times H^{0.3}$$

$$BSA=0.008883 \times W^{0.444} \times H^{0.663}$$

$$BSA=0.007241 \times W^{0.425} \times H^{0.725}$$

$$BSA=0.000975482 \times W^{0.46} \times H^{1.08} \text{ (formula exclusively used for women)}$$

$$BSA=0.000579479 \times W^{0.38} \times H^{1.24} \text{ (formula exclusively used for men)}$$

The patient-specific physiological parameters and/or the patient-derived quotients determined based thereon can be used, in combination with the heart rate as envisaged herein to determine the optimal volume of contrast medium.

In particular embodiments, the optimal volume of contrast medium is determined directly based on these factors. Such methods may be based on the desired amount of contrast agent to be administered for the patient, which is then translated into an optimal volume of contrast medium taking into account on the density of the contrast agent in the medium, and physiological parameters including the size of the patient and the heart rate of the patient.

As indicated above, additionally or alternatively, the determination of the optimal volume of contrast medium may further comprise one or more parameters related to the specifics of the imagining method. Examples of such parameters are the radiographic tube voltage of the CT scanner (typically expressed in Kv). Indeed, generally the lower the tube voltage, the more limited the amount of contrast medium that can be injected. Further non-patient specific factors may include the type of scanner and other factors related to the injection process. It will be understood that a further parameter which may play a role is the concentration of the contrast agent in the contrast medium (typically expressed as mg/ml). Indeed, where the concentration is higher, less of the medium will need to be used.

However, it is envisaged that typically for one imaging set-up, the nature of the contrast medium will be fixed or at least limited (in that the institution where the scanning instrument is being used will generally use only one or a limited number of commercially available contrast media. In this regard it is envisaged that this parameter may be replaced by a fixed factor for each medium. This also applies for the device-related parameters.

In particular embodiments of the methods envisaged herein, the optimal volume of contrast medium is determined starting from an initial volume of contrast medium, which is then further adjusted based on the heart rate and optionally one or more additional patient-specific physiological parameters. Said initial volume may be a standard volume, which has been determined based on experience by the skilled person. Most hospitals have established standard volumes of contrast medium to be administered to a patient. Typically, different standard volumes are applied depending on the region of the body of interest (e.g. thorax, abdomen, legs etc.). The standard volume may further be different for adults and children or for males and females. For instance, in a particular hospital, the standard volume for a CT scan of the thorax-abdomen may be 120 ml for an adult, or for a CT scan of only the thorax may be 80 ml for an adult. Thus, in particular embodiments, the optimal volume of contrast medium to be administered is determined starting from the standard volume.

In particular embodiments of the methods envisaged herein, the optimal volume of the contrast medium to be administered is determined based on an initial volume of contrast medium which is calculated based on patient-specific physiological parameters. Indeed, patient-specific physiological parameters (other than the heartbeat), such as those described above.

In particular embodiments, the initial volume of the contrast medium is determined based on body weight (in air). For instance it can be envisaged that in particular embodiments, the initial volume is determined based on body weight, e.g. a fixed volume of contrast medium/kg body weight, or based on ranges of body weight etc.

In further particular embodiments the initial volume of contrast medium is determined on more than one patient-specific parameter, such as the combination of three, four, five or more parameters. In particular embodiments, the initial volume is calculated based on the patient's body weight (in air) and height.

In particular embodiments, the methods encompass determining the patient's height, skinfold measurements and girth measurements to determine the muscle mass wherein said muscle mass is used to determine said initial volume of contrast medium.

In particular embodiments, the methods encompass determining the patient's skinfold measurements and/or the patient's girth measurements and these are used to determine the body fat percentage wherein said body fat percentage is used to determine said initial volume of contrast medium. In particular embodiments, the patient's weight in air; weight in water and the residual lung volume are determined and used to determine the body density; and wherein said body density, is used to determine said initial volume of contrast medium. In particular embodiments, the one or more patient-specific physiological features are used to determine one or more patient-derived quotients, such as described above. The one or more patient-derived quotients can then be used to determine the initial volume of contrast medium. More particularly, it is envisaged that, in particular embodiments of the methods envisaged herein, the patient's body weight and height is used to determine Body surface area (BSA), which is then used to determine the initial volume of contrast medium. In particular embodiments, the BSA is multiplied by a factor C which represents the amount of contrast medium to be administered per $m^2$ surface of the body. This factor C can be a standard value which is determined within a care center based on experience and/or scientific calculations. It is noted that this factor may also depend on the contrast medium used. Typically, for the currently most commonly used contrast media, this factor C is between 40-50 ml/$m^2$. In particular embodiments, factor C is 42-47 ml/$m^2$, more particularly 45 ml/$m^2$. This factor C can be determined based on the amount of contrast agent considered to be required to obtain the desired image quality, whereby C is then derived for a specific (commercially available) contrast medium based on the density of the contrast agent in the medium. Studies which describe the determination of the amount of contrast agent e.g. mg Iodine) to be administered per $m^2$ include but are not limited to Yanaga et al. 2010, AJR, 194:903-908.

Thus, in particular embodiments, the methods envisaged herein comprise the steps of: (a) determining one or more patient-specific physiological parameters, said one or more patient-specific physiological parameters comprising at least the patient's heart rate;

(b) calculating an initial volume of contrast medium, and;
(c) adjusting the initial volume of contrast medium on the basis of the patient's heart rate, thereby determining the optimal volume of contrast medium.

The adjusting of the initial volume of contrast medium on the basis of the patient's heart rate, according to step (c), may be achieved by increasing said initial volume of contrast medium; by decreasing said initial volume of contrast medium or by maintaining said initial volume of contrast medium.

The increase or decrease in volume of contrast medium may be linear, logarithmic or exponential. It may be continuous or incremental.

In particular embodiments, the determination of whether the initial volume of contrast medium is to be increased or reduced, is performed by the use of one or more predetermined threshold levels. Such a threshold level may be predetermined in function of the patient's heart rate. Thus, in particular embodiments of the methods envisaged herein the initial volume of contrast medium (as determined in step (b) above) is decreased in volume, if said patient's heart rate is below a predetermined threshold level and the initial volume of contrast medium is increased in volume, if said patient's heart rate is above said predetermined threshold level.

In particular embodiments of the methods envisaged herein, the initial volume of contrast medium is decreased in volume, if said patient's heart rate is below or equal to a predetermined threshold level; and the initial volume of contrast medium is increased in volume, if said patient's heart rate is above said predetermined threshold level. Alternatively, in particular embodiments of the methods envisaged herein, the initial volume of contrast medium is decreased in volume, if said patient's heart rate is below a predetermined threshold level; and the initial volume of contrast medium is increased in volume, if said patient's heart rate is above or equal to said predetermined threshold level.

The specific values of the thresholds and the extent to which the volume is to be increased or decreased may be determined by the skilled person and may be influenced by different factors such as the nature of the contrast medium, the measuring apparatus etc. In particular embodiments, the predetermined threshold level is chosen in the range of 49 to 71 beats-per-minute. In further particular embodiments, the threshold level is chosen in the range of 51 to 69 beats-per-minute; most preferably, said threshold level is chosen in the range of 55 to 65 beats-per-minute. In particular embodiments, the decrease in volume of the initial volume of contrast medium if the heart rate is below the threshold is in the range of 1 to 19 ml. In particular embodiments, the decrease in volume of the initial volume of contrast medium is chosen in the range of 5 to 15 ml. More particularly, said decrease in volume of the initial volume of contrast medium is chosen in the range of 7 to 13 ml. In particular embodiments, the increase in volume of the initial volume of contrast medium, if the heart rate is above the threshold is in the range of 1 to 40 ml. In particular embodiments said increase in volume of the initial volume of contrast medium is chosen in the range of 5 to 35 ml. In particular embodiments, the increase of volume of the initial volume of contrast medium is chosen in the range of 10 to 30 ml. It will be clear to the skilled person that the above ranges may be combined as appropriate.

In particular embodiments of the methods envisaged herein, the determination of whether the initial volume of contrast medium is to be increased or reduced, on the basis of the patient's heart rate, is achieved by the use of more than one predetermined threshold levels. In particular embodiments of the methods envisaged herein, at least two predetermined threshold levels are used, wherein said initial volume of contrast medium is decreased in volume if said patient's heart rate is below or equal to a first predetermined threshold level; and said initial volume of contrast medium is increased in volume if said patient's heart rate is above or equal to a second predetermined threshold level and the initial volume of contrast medium is not adjusted if the patient's heart rate is situated between said first and second threshold levels. Again, the different thresholds can be determined by the skilled person, and may be influenced by different factors.

In particular embodiments, of the methods envisaged herein the first predetermined threshold level is chosen in the range of 50 to 60 beats-per-minute; in particular embodiments the second predetermined threshold level is chosen in the range of 61 to 71 beats-per-minute. In further particular embodiments, the first predetermined threshold level is chosen in the range of 50 to 60 beats-per-minute, and the second predetermined threshold level is chosen in the range of 61 to 71 beats-per-minute and the initial volume of contrast medium is not adjusted if the patient's heart rate is situated between said first and second threshold levels. In further particular embodiments, the first predetermined threshold level is chosen in the range of 52 to 58 beats-per-minute, more particularly in the range of 53 to 57 beats-per-minute; in further particular embodiments, the second predetermined threshold level is chosen in the range of 63 to 69 beats-per-minute, more particularly in the range of 64 to 68 beats-per-minute. Again, it will be understood to the skilled person that said ranges can be combined. Again, as detailed above however, such threshold levels can be established by the skilled person and the exemplary values should not be considered as critical to the methods envisaged herein.

As detailed above, in particular embodiments, the increase is linear and may be with predefined increments. Again, it will be understood that the actual values of the increments are not critical to the methods envisaged herein. Exemplary values are provided hereinafter. In particular embodiments of the methods described above, the decrease in volume of the initial volume of contrast medium is chosen in the range of 1 to 19 ml and the increase in volume of the initial volume of contrast medium is chosen in the range of 1 to 40 ml. More particularly, the decrease in volume of the initial volume of contrast medium is chosen in the range of 5 to 15 ml and the increase in volume of the initial volume of contrast medium is chosen in the range of 5 to 35 ml. In further particular embodiments, the decrease in volume of the initial volume of contrast medium is chosen in the range of 7 to 13 ml and the increase in volume of the initial volume of contrast medium is chosen in the range of 10 to 30 ml. In particular embodiments of the methods envisaged herein, the initial volume of contrast medium is adjusted according to table I.

TABLE I

Exemplary heart rate threshold levels.

| Heart rate (beats-per-minute) | Optimal volume of contrast medium |
|---|---|
| ≤55 | Initial volume − at least 10 ml |
| 56-65 | Initial volume + (−9 to +9 ml) |
| 66-75 | Initial volume + 10 to 19 ml |
| 76-90 | Initial volume + 20 to 24 ml |
| 91-105 | Initial volume + 25 to 30 ml |
| ≥106 | Initial volume + 30 ml or more |

In further particular embodiments of the methods envisaged herein, the initial volume of contrast medium is adjusted according to table II.

TABLE II

Exemplary heart rate threshold levels.

| Heart rate (beats-per-minute) | Optimal volume of contrast medium |
|---|---|
| ≤55 | Initial volume − 10 ml |
| 56-65 | Initial volume + 0 ml |
| 66-75 | Initial volume + 10 ml |
| 76-90 | Initial volume + 20 ml |
| 91-105 | Initial volume + 25 ml |
| ≥106 | Initial volume + 30 ml |

It is noted that, as indicated above, the calculation of the optimal volume of contrast medium is intended to reflect the total amount of undiluted contrast medium which should be administered to the patient in order to obtain the achieved effects. However, in particular embodiments, it may be of interest to further dilute the contrast medium prior to administration. This can be the case e.g. where adverse reaction of the patient against the contrast medium is expected. Indeed, in some embodiments, the methods envisaged herein may be followed by a step of diluting the optimal volume of contrast medium obtained in step (c). In such cases the physician may decide to administer a volume of diluted contrast medium which corresponds to the optimal volume as determined in step (c), but, wherein the contrast medium is diluted with another fluid (such as saline). In these embodiments, the actual volume of fluid administered to the patient will be the same as the volume which was determined to be the optimal volume in step (c). Alternatively, the physician may consider to administer the optimal volume of contrast medium determined in step (c) but to nevertheless dilute this volume with another fluid. Thus, in these latter embodiments, the actual volume of fluid to be administered to a patient may differ from the optimal volume of contrast medium determined in step (c).

The dilution of the optimal volume of contrast medium may be performed by any method known in the art. In some embodiments, the contrast medium is diluted with the addition of physiological water (saline). In further embodiments, the contrast medium is diluted with a fluid selected from a buffer or blood. In particular embodiments, the optimal volume is not diluted or diluted only to a limited extent in order to avoid the generation of artifacts on the image.

As indicated above, the exact nature of the contrast medium is not critical to the methods envisaged herein. In particular embodiments, the contrast medium comprises a radio contrast agent.

As used herein, the term "radio contrast agent" refers to a compound used to improve the visibility of internal bodily structures in X-ray based imaging techniques. As used herein, the term "X-ray based imaging techniques" refers to a technique that uses X-rays to view the human body. X-ray based imaging techniques suitable for the present method include, computed tomography (CT scanning) and radiography. Preferably, CT scanning is used. Radio contrast agents suitable for the present method include iodine and barium compounds.

The present application also encompasses the method according any of the embodiments described herein, wherein the radio contrast agent used is an iodine-based contrast agent.

Iodine-based contrast media are usually classified as ionic or non-ionic, depending on whether the iodine is (covalently) bound to an organic compound (non-ionic iodine-based contrast media) or to an ionic compound (ionic iodine-based contrast media). Since the iodine is covalently bound to the non-ionic iodine-based contrast media, they do not dissociate into component molecules. While both ionic and non-ionic contrast media are envisaged to be suitable, in practice non-ionic, low-osmolar media are currently preferred. Table III shows some suitable iodine-based contrast media.

TABLE III

Exemplary Iodine-based contrast agents.

| Compound type | Name |
| --- | --- |
| Non-ionic | Iopamidol (Isovue 370) |
| Non-ionic | Iohexol (Omnipaque 350) |
| Non-ionic | Ioxilan (Oxilan 350) |
| Non-ionic | Iopromide (Ultravist 370) |
| Non-ionic | Iodixanol (Visipaque 320) |
| Non-ionic | Iomeron (Iomeprol 300, 350, 400) |

Preferably, the iodine-based contrast media of the present application are administered intravenously.

The methods envisaged herein are of use in detection methods where the administration of a contrast agent is required. The methods have the advantage that the optimal volume of contrast medium to be administered to a patient is determined on a personalized way, based on the patient-specific physiological parameters which allows the radiologist to use enough contrast medium to provide an accurate diagnosis, while at the same time, the number of adverse reactions that said contrast medium causes to a patient is kept to a minimum.

Indeed, one of the objects of the methods and tools envisaged herein is to allow the adjustment of the volume of contrast medium without affecting the quality of the image obtained. Typically, the quality of the image can be ascertained by detection of the arteries and veins in the liver, which is generally used as a standard.

Thus the application envisages methods for imaging a body part of a patient using a technology involving administration of a contrast medium, wherein said methods encompass the step of determining the optimal volume of contrast medium for said patient by a method according to an embodiment described herein. The methods are of particular interest to reduce toxicity effects of the contrast medium. Thus, the application also provides methods for reducing the toxicity or adverse side effects of a contrast medium in a patient which comprises the step of determining the optimal volume of contrast medium for said patient by a method according to an embodiment described herein. The methods as envisaged herein are thus of particular interest in the imaging of a body part of a patient which is susceptible to the toxicity or adverse side effects of a contrast medium. Thus in particular embodiments, the patient envisaged is a patient which is susceptible to the toxicity or adverse side effects of a contrast medium. In further particular embodiments, the patient is a patient of which the renal function is impaired. In further particular embodiments, the patient is a patient at risk of impaired renal function. In further particular embodiments, the patient is a patient in need of multiple scans within a limited time frame and/or repeated scans over a prolonged period of time.

The methods of determining the optimal volume of contrast medium to be administered to a patient as described herein, have the further advantage that the results of different scans, performed on one patient are easier to compare, even if the anthropometric measurements of the patient have changed. Thus in particular embodiments, the patient is a patient which is subject to repeated scans over a prolonged period of time, more particularly if said patient is expected to vary in anthropometric measurements.

Administering a personalized amount of optimal volume of contrast medium to a patient, according to the present application, has the further advantage that the scans performed are more accurate, thereby minimizing the need to repeat a scan due to poor contrast of the images.

The method of determining the optimal volume of contrast medium to be administered to a patient as described herein, can in particular embodiments be of interest for pediatric patients. Thus, in particular embodiments, the patient is a pediatric patient. It will be understood however, that for children, more particularly for patients under the age of 16, where the methods involve the determination of an initial volume of contrast medium, the actual value of the "initial volume" will differ from that used in adults and/or the method for determining said initial volume may differ from that used for adults. Indeed, it will be understood by the skilled person that methods which are based on BSA values are less suitable for children.

The method of determining the optimal volume of contrast medium to be administered to a patient as described herein, by taking into account the patient's heart rate, has the further advantage that it takes into account the physiological condition of the patient at the time of taking the scan. Thus, factors such as nervousness or certain physiological conditions which may influence the suitability of the volume to be administered are incorporated due to the fact that they are reflected in the heart rate.

The nature of the image to be taken or its final purpose is not critical for the methods described herein. It will be understood to the skilled person that the methods envisaged herein are of particular interest for situations in which automated intravenous injection of a contrast medium is envisaged. In particular embodiments, the methods are applied in the context of CT screenings, such as not limited to oncological screenings. Such screenings may be performed as a result of the determination of one or more primary symptoms or may be systematic screenings of high risk patients. For instance the methods are of interest in the screening for lung cancer in individuals at high risk of developing the disease due to smoking. In particular embodiments, the methods envisaged herein are used to determine the optimal volume of contrast medium to be administered for imaging a body part other than the heart.

In particular embodiments, the methods envisaged herein are used to determine the optimal volume of contrast medium to be administered for imaging a body part other than the heart (i.e. the heartchambers) and the arteries and veins in the direct vicinity thereof. In particular embodiments, the methods are applied for CT scans of one or more of thorax, abdomen and lower legs. In further particular embodiments, the methods are applied for thorax/abdomen CT scans. In particular embodiments the methods are envisaged for imaging the lungs and/or the digestive tract. In particular embodiments the methods are envisaged for imaging one or more of oesophagus, stomach, intestines (small and/or large bowel), bladder, liver, spleen, uterus.

The present application also encompasses computer methods which when loaded on a computer ensure the methods envisaged herein. Indeed, this can be ensured by computer programs comprising the instructions to carry out the methods as described herein. Such computer methods may be stored on a computer readable medium. In particular embodiments, the computer is provided with a screen which outputs the optimal volume of contrast medium.

The application also provides devices for injecting a contrast medium into a patient and/or controllers for such devices. Such devices or controllers may comprise or be driven by a computer program capable of determining the optimal volume of contrast medium for the patient based on the physiological parameters of the patient including the heart rate, as detailed above. Said latter parameters can be inputted to the device directly from a detection tool coupled to the device (such as a heart rate monitor) and/or can be downloaded from the patient's file or be inputted manually. In particular embodiments, the device is an injector.

In particular embodiments, the device or controller comprises an interface which allows the user to select one or more variables. In particular embodiments, the variables may include the body part of which an image is desired, the nature of the image (e.g. arterial or venal scan), the speed of administration and the algorithm to be used for determining the optimal volume of contrast medium. In particular embodiments, the variables include the initial volume or the algorithm to be used to calculate the initial volume. In particular embodiments, the interface may further allow for the option to adjust the final volume manually. In particular embodiments, where the device is configured to initiate actual scanning, the interface may also be configured to allow selection of the timing of the start of the scan after injection.

Indeed, it is envisaged that the nature of the scanning device may influence the envisaged timing of the start of the scan. More particularly, where the scanning time is longer (typically for older devices), an adjustment of the scan start time may be required to ensure an optimal scanning image. Moreover, the optimal time to start scanning may also be influenced by the organ to be imaged. Indeed, while in particular embodiments for an abdomen/thorax scan, the timing will be 90 seconds after administration of contrast medium, the user may want to adjust this. In particular embodiments, where the device is configured to allow dilution of the contrast medium prior to administration, the interface may be configured to allow the user to ensure that the medium is diluted prior to administration.

The following examples are provided for the purpose of illustrating the present invention and by no means should be interpreted to limit the scope of the present invention.

EXAMPLES

Example 1

Determination of the Initial Volume of Contrast Medium.

The following patient-specific physiological parameters were measured:
Height: 183 cm;
Weight: 77 kg;
And the body surface area (BSA) was calculated as patient-derived quotient:

$$BSA=[(height \times weight)/3600]^{0.5}$$

$$BSA=[(183 \times 77)]/3600]^{0.5}$$

$$BSA=1.957 \ m^2$$

Finally, the BSA was used to calculate the initial volume of contrast medium according to the following formula:

$$\text{Initial volume of contrast medium}=BSA \times C$$

wherein C is the volume of contrast medium per $m^2$ of body surface, needed to scan the specific body region. In the present case, the value C was chosen as 45 ml/$m^2$.

$$\text{Initial volume of contrast medium}=(1.957) \times (45)$$

Initial volume of contrast medium=88 ml (since the value has to be rounded up or down).

Example 2

Determination of the Optimal Volume of Contrast Medium Based on an Initial Volume.

The patient's heart rate was measured:
Heart rate: 72 beats-per-minute
The initial volume of contrast medium, calculated in Example 1 to be 88 ml, was then adjusted in function of the heart rate, and according to Table II:

TABLE II

Heart rate threshold levels.

| Heart rate (beats-per-minute) | Optimal volume of contrast medium |
|---|---|
| ≤55 | Initial volume − 10 ml |
| 56-65 | Initial volume + 0 ml |
| 66-75 | Initial volume + 10 ml |
| 76-90 | Initial volume + 20 ml |
| 91-105 | Initial volume + 25 ml |
| ≥106 | Initial volume + 30 ml |

Thus, in the present case, based on the heart rate, the optimal volume was adjusted as follows:

$$\text{Optimal volume of contrast medium}=88+10$$

$$\text{Optimal volume of contrast medium}=98 \ ml.$$

The invention claimed is:

1. A controller for a device for administering contrast medium comprising radio contrast agent into a patient using an injector, the device or controller comprising:
  (a) an input allowing input of one or more patient-specific physiological parameters, the one or more patient-specific physiological parameters comprising at least the patient's heart rate, length and weight;
  (b) a processor communicatively coupled to the input configured to calculate an optimal volume of contrast medium based on the one or more patient-specific physiological parameters; and
  (c) a connection to the injector configured to control the volume of contrast medium to be injected into the patient prior to administration, based on the optimal volume calculated by the processor;

wherein the controller is configured to use the length and weight of the patient to determine the Body Surface Area (BSA) of the patient and the optimal volume of contrast medium is calculated based both on the BSA and the heart rate of the patient; and wherein the calculation of the optimal volume of contrast medium comprises starting from an initial volume of contrast medium and adjusting the volume based on the heart rate of the patient.

2. The controller according to claim 1, wherein the processor makes use of ranges with threshold values based on which the initial volume is either increased or decreased.

3. The controller according to claim 2, wherein the processor makes use of ranges with threshold values based on which the initial volume is either increased or decreased and wherein the calculation is based on at least two predetermined threshold values, whereby the initial volume of contrast medium is decreased when the heart rate of the patient is lower or equal to the first previously determined limit value and whereby the initial volume of contrast medium is increased when the heart rate of the patient is higher or equal to the second threshold value.

4. The controller according to claim 3, wherein the processor makes use of ranges with the following heart rate threshold values based on which the initial volume is either increased or decreased:

| Heart rate (beats-per-minute) | Optimal volume of contrast medium |
| --- | --- |
| ≤55 | Initial volume − 10 ml |
| 56-65 | Initial volume + 0 ml |
| 66-75 | Initial volume + 10 ml |
| 76-90 | Initial volume + 20 ml |
| 91-105 | Initial volume + 25 ml |
| ≥106 | Initial volume + 30 ml. |

5. The controller according to claim 3, wherein the first predetermined threshold level is chosen in the range of 50 to 60 beats-per-minute and wherein the second predetermined threshold level is chosen in the range of 61 to 71 beats-per-minute.

6. The controller according to claim 5 wherein the decrease in volume of the initial volume of contrast medium is chosen in the range of 1 to 19 ml and wherein the increase in volume of contrast medium is selected to be in the range of 1 to 40 ml.

7. The controller according to claim 1, wherein, the optimal volume of contrast medium is further calculated based on one or more patient-derived quotients selected from body mass index; ideal body weight; lean body weight; adjusted body weight and body surface area.

8. The controller according to claim 1, wherein, the patient-specific parameters further comprise one or more parameters selected from age, gender, estimated glomerular filtration rate (eGFR) and cardiac output (CO).

9. The controller according to claim 1, wherein the processor further takes into account one or more non-patient-specific parameters to calculate the optimal volume of contrast medium, the one or more non-patient-specific parameters being selected from the tube-voltage of the scanner instrument to be used for imaging and the type of scanner used for imaging.

10. A contrast delivery system comprising the controller of claim 1 and an injector.

11. A method for determining the optimal volume of contrast medium comprising radio contrast agent to be administered to a patient prior to administration, comprising the steps of:

(a) inputting one or more patient-specific physiological parameters to an input of a controller, the one or more patient-specific physiological parameters comprising at least the patient's heart rate, length and weight, wherein the length and weight of the patient are used by a processor of the controller communicatively coupled to the input to determine the Body Surface Area (BSA) of the patient and the optimal volume of contrast medium is calculated based both on the BSA and the heart rate of the patient;

(b) calculating by the processor the optimal volume of contrast medium based on the one or more patient-specific physiological parameters; and (c) adjusting by the processor the volume of contrast medium to be administered to the patient to correspond with the optimal volume of contrast medium;

wherein the calculation of the optimal volume of contrast medium and the adjustment of the volume of contrast medium to be administered comprises starting from an initial volume of contrast medium and adjusting the volume based on the heart rate of the patient, and wherein the controller is for a device for administering contrast medium comprising radio contrast agent into a patient using an injector.

12. The method of claim 11 wherein the calculation of the optimal volume of contrast medium comprises starting from an initial volume of contrast medium and adjusting the volume based on at least two predetermined threshold values, whereby the initial volume of contrast medium is decreased when the heart rate of the patient is lower or equal to the first previously determined limit value and whereby the initial volume of contrast medium is increased when the heart rate of the patient is higher or equal to the second threshold value.

13. The method of claim 11, wherein:

the controller further comprises a connection to the injector configured to control the volume of contrast medium to be injected into the patient prior to administration, based on the optimal volume calculated by the processor.

14. A tangible non-transitory computer-readable medium comprising a computer program comprising instructions for carrying out, when loaded on a computer:

(a) determine one or more patient-specific physiological parameters, the one or more patient-specific physiological parameters comprising at least the patient's heart rate, length and weight, wherein the length and weight of the patient are used to determine the Body Surface Area (BSA) of the patient and the optimal volume of contrast medium is calculated based both on the BSA and the heart rate of the patient;

(b) calculated the optimal volume of contrast medium based on the patient-specific physiological parameters;

(c) adjust the volume of contrast medium to be administered to the patient to correspond with the optimal volume of contrast medium; and wherein the calculation of the optimal volume of contrast medium comprises starting from an initial volume of contrast medium and adjusting the volume based on the heart rate of the patient.

15. The tangible non-transitory computer-readable medium according to claim 14, wherein the computer is a controller for a device for administering contrast medium comprising radio contrast agent into a patient using an injector, the controller comprising:
(a) a controller input allowing input and determination of the one or more patient-specific physiological parameters;
(b) a controller processor communicatively coupled to the controller input configured to calculate the optimal volume of contrast medium based on the one or more patient-specific physiological parameters; and
(c) a controller connection to the injector configured to adjust the volume of the contrast medium to be injected into the patient prior to administration, based on the optimal volume calculated by the controller processor.

* * * * *